United States Patent [19]

Shippert

[11] Patent Number: 4,568,332
[45] Date of Patent: Feb. 4, 1986

[54] MEDICAL INSTRUMENT FOR SUCTION LIPECTOMY

[76] Inventor: Ronald D. Shippert, 4975 S. Albion St., Littleton, Colo. 80121

[21] Appl. No.: 549,773

[22] Filed: Nov. 8, 1983

[51] Int. Cl.⁴ .............................................. A61M 1/00
[52] U.S. Cl. ..................... 604/119; 433/91; 433/95; 604/264; 604/276
[58] Field of Search ............... 128/304; 206/374, 375; 433/91, 95; 604/902, 48, 51, 54, 73, 93, 94, 118, 119, 173, 264, 275, 276, 32; 251/208, 209, 293, 311

[56]  References Cited

U.S. PATENT DOCUMENTS

| | | | |
|---|---|---|---|
| 2,449,497 | 9/1948 | McLeod | 128/276 |
| 2,531,730 | 11/1950 | Henderson | 128/276 |
| 3,071,402 | 1/1963 | Lasto et al. | 294/64 |
| 3,146,987 | 9/1964 | Krayl | 604/119 |
| 3,797,486 | 3/1974 | Shaps | 604/93 |
| 3,889,682 | 6/1975 | Denis et al. | 604/119 |
| 3,902,494 | 9/1975 | Haberlen et al. | 128/275 |
| 3,955,579 | 5/1976 | Bridgman | 128/304 |
| 3,963,028 | 6/1976 | Cooley et al. | 128/276 |
| 4,022,218 | 5/1977 | Riddick | 128/350 |
| 4,049,000 | 9/1977 | Williams | 128/276 |
| 4,219,021 | 8/1980 | Fink | 128/214 |
| 4,230,128 | 10/1980 | Aramayo | 128/763 |

OTHER PUBLICATIONS

Lorenz Oral Surgery Suction System, 1983.
MEDICALEX-USA Aspirator Type 2004, Industry, California.
API Irrigation and Suction Tube-Suction Tube-Anthony Products, Indianapolis, Ind. 46226.

Primary Examiner—J. L. Kruter
Attorney, Agent, or Firm—Sheridan, Ross & McIntosh

[57]  ABSTRACT

A medical instrument for removing fat from inside a human body is provided wherein first and second projections, each adapted to be connected to a suction probe or a suction tube, are located at one end of a hollow body.

19 Claims, 12 Drawing Figures

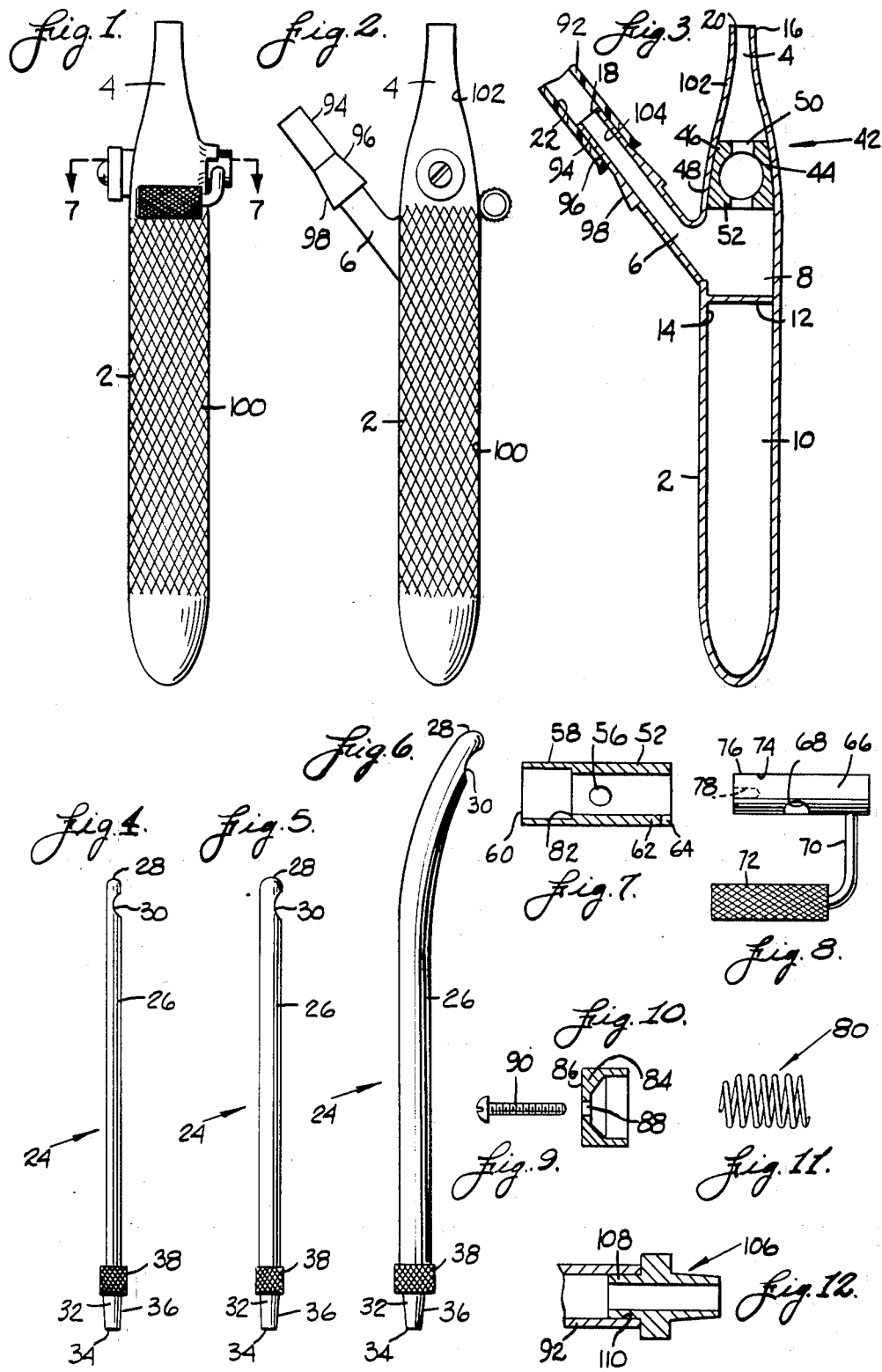

MEDICAL INSTRUMENT FOR SUCTION LIPECTOMY

FIELD OF THE INVENTION

This invention is directed to a medical instrument and in particular to a medical instrument for removing fat from within the human body.

BACKGROUND OF THE INVENTION

In recent years, a new type of plastic surgery has been introduced wherein fat is removed from within the human body by using a thin metal suction tube that is introduced through a tiny skin incision and repeatedly thrust through the unwanted fat to break up the fat globules. Vacuum is applied when it is desired to remove the loosened fat globules. The medical instrument for performing such an operation comprises a hollow body for holding by the hand. At one end, a suction probe is attached to the body and the other end of the body is connected to a source of vacuum. The probe is used to break the fat globules and then suction is applied to suck the loosened fat globules out of the body. The probing and sucking is repeated until the desired amount of fat is removed. In some cases, the operation will require hours of probing and sucking. In the past, a foot control valve has been used to apply the suction even though medical instruments used in oral surgery, such as those marketed by Lorenz, have had suction control valves associated with a hollow body.

BRIEF DESCRIPTION OF THE INVENTION

The medical instrument of this invention comprises a hollow body having a first and a second projection extending therefrom. The first and second projections are provided with means so that they may be readily connected to a suction probe or to a source of vacuum. A control valve is associated with the body so that the first or second projection may be quickly and easily connected to the vacuum source.

In the preferred embodiment of the invention, the hollow body is divided into a first and a second section. The longitudinal axes of the first section and the first projection are in alignment while the longitudinal axis of the second projection extends at an angle of about 45° to the first section. In normal practice, a suction probe is connected to the first projection and end one of a transparent tube is connected to the second projection with the other end of the tube connected to a source of vacuum. A control valve is associated with the hollow body so that the connection to the vacuum source may be opened and closed readily. Since the vacuum tube is located on the first or second projection, the surgeon will immediately detect any bleeding so that the operation may be halted to enable the surgeon to stop the bleeding. In use, a small incision is made in the skin and the suction probe is inserted therethrough. With the control valve in the off position, force is applied to the suction probe to break down the fat globules. When sufficient fat globules have been broken down, the control valve is moved to the open position and the vacuum sucks out the broken down fat globules. This is repeated as often as it is required to remove the desired quantity of fat.

It is an object of this invention to provide a medical instrument useful in removing fat from within the human body wherein all the major components are adjacent one end of a body.

It is another object of this invention to provide a medical instrument useful in removing fat from within the human body wherein the fat globules as they are being removed are readily observable.

It is a further object of this invention to provide a medical instrument useful in removing fat from the human body where the mode of the application of the force by the operator may be readily varied.

Other features and advantages of the invention will be apparent from the following more particular description of preferred embodiments as illustrated in the accompanying drawings in which like reference characters refer to the same parts throughout the various views. The drawings are not necessarily to scale, emphasis instead being placed upon illustrating the principles of the invention.

BRIEF DESCRIPTION OF THE DRAWINGS

FIG. 1 is a front elevational view of a portion of a medical instrument of this invention;

FIG. 2 is a side elevational view of FIG. 1;

FIG. 3 is a cross-sectional view of FIG. 2; with portions of the valve excluded therefrom.

FIGS. 4, 5 and 6 are plan views of some suction probes useful with a medical instrument of FIG. 1;

FIG. 7 is a cross-sectional view of one portion of the valve taken on line 7—7 of FIG. 1;

FIG. 8 is a plan view of another portion of the valve;

FIGS. 9, 10 and 11 are plan views of other portions of the valve; and

FIG. 12 is a modification of the invention.

DETAILED DESCRIPTION OF THE DRAWING

A preferred embodiment of the invention, as illustrated in FIGS. 1, 2 and 3, comprises a body 2 having a first projection 4 extending therefrom and a second projection 6 extending at an angle therefrom. The body 2 is divided into two hollow sections 8 and 10 by the member 12 which is secured to the inner surface 14 of the body 10 so that the section 8 is sealed off from the section 10. The first projection 4 has circular opening 16 adjacent the end thereof and the second projection 6 has circular opening 18 adjacent the end thereof. The inner surface 20 of the first projection 4 adjacent the opening 16 and the inner surface 22 of the second projection 6 are generally cylindrical in cross section.

A variety of suction probes 24 are illustrated in FIGS. 4, 5 and 6. It is to be understood that an infinite number of suction probes differing in size and shape may be used. Each suction probe 24 has a hollow tubular body 26 closed at one end 28. An opening 30 is provided in the sidewall of the body 26 adjacent the end 28. The other end 32 of the suction probe 24 is provided with an opening 34. The outer surface 36 of the other end 32 is conical with the smallest diameter adjacent the opening 34. An annular ring 38 having a knurled surface is secured to the body 26 adjacent the other end 32.

The valve 42 is illustrated in FIGS. 3, 7, 8, 9, 10 and 11 and comprises a unit 44 having an outer surface 46 shaped to unite with the inner surface 48 of the first projection 4. The unit 44 is secured to the first projection 4 so as to form a complete annular seal therebetween. The unit 44 has an annular passageway 50 extending therethrough. A hollow tube 52 is secured to the unit 44. The hollow tube 52 is provided with aligned openings 56 passing through the sidewall of the hollow tube 52. The hollow tube 52 is secured to the unit 44 so that the openings 56 are aligned with the passageway 50. At one end 58, the hollow tube 52 is provided with a bore 60 and at the other end 62, a portion of the sidewall is removed to form shoulders 64, each for a purpose to be described below. The means for opening and closing the valve 42 comprises a solid tubular stem 66 having a passageway 68 extending therethrough. A handle 70 having a knob 72 having a knurled surface is secured to the stem 66. The knob 72 extends in a direction parallel to the extent of stem 66. The outer surface 74 of the stem 66 tapers gradually with the smallest diameter being adjacent the end 76. A threaded bore 78 is provided in the one end 76 of the stem 66. In operational association, the stem 66 is inserted into the hollow tube 52 so that the openings 56 will be aligned with the passageway 68 when the valve 42 is in the opened position.

The means for holding the stem 66 in the tube 52 and permitting relative rotation between the stem 66 and the tube 52 is illustrated in FIGS. 9, 10 and 11. A spring 80 is dimensioned to fit inside the bore 60 and abut against the shoulder 82. A hollow cylindrical member 84 having a base 86 with a central opening 88 is also dimensioned to fit inside the bore 60 and abut against the shoulder 82. The member 84 has internal dimensions so that the spring 80 will fit inside the member 84. A threaded screw 90 passes through the opening 88 and is threadedly engaged in the threaded bore 78. The screw 90 is adjusted until the proper amount of frictional force is established between the stem 66 and the tube 52 so that the valve 42 may be rotated to an opened or closed position and be retained in either position by the frictional force. The valve is in an opened or closed position when the handle 70 abuts against either of the shoulders 64.

In operation, a suction probe 24 is inserted through the opening 16 in the first projection 4 until the outer surface 36 is in engagement with the inner surface 20. Sufficient force is applied to the probe 24 so that the probe 24 will remain in position while being used in the operation. A transparent hollow tube 92 is pushed over the outer surface 94 of the second projection 6 and partially up the outer surface 96 of a conical ring 98 secured to the outer surface of the second projection 6. The other end of the tube 92 is secured to a source of vacuum (not shown). The valve 42 is rotated to a closed position wherein the passageway 68 is not exposed to any portion of either opening 56 by movement of the knob 72. The vacuum source is then turned on. A small incision is made in the skin of the patient. The body 2, having a knurled surface 100, is grasped by the physician and inserted through the incision into the patient. Force is applied to the probe 24 so that the end 28 thereof will break down any fat it contacts into fat globules. When sufficient fat globules have been broken down, the knob 76 is pushed and the stem 66 is rotated to an opened position with passageway 68 aligned with the openings 56. In this opened position, the opening 30 is connected to the vacuum source through a continuous passageway comprising the hollow body 26, the opening 34, the opening 16, the passageway 50, the openings 56 and passageway 68, the hollow section 8, the opening 18 and the transparent tube 92. Since the transparent tube 92 is located adjacent the suction probe 24, the physician may readily observe the broken down fat globules being removed. If excessive bleeding is observed, the valve 42 is moved to a closed position and the suction probe 24 is removed so that the physician may stop the excessive bleeding. In the preferred embodiment the operation is performed in an intermitted mode with the valve 42 in a closed position while the suction probe 24 is being used to break down the fat into fat globules or, if desired, in a continuous mode with the valve 42 always opened. If the physician tires during the operation, the positions of the suction probe 24 and the transparent tube 92 are reversed so that the suction probe 24 is retained in the second projection 6 and the transparent tube is over the outer surface 102 of the first projection 4. The outer surface 102 is conical with dimensions similar to the outer surface 96 of the ring 98. The inner surface 104 of the second projection 6 is dimensioned similarly to the inner surface 20 so as to be in engagement with the outer surface 36 of the end 32 of the suction probe 24.

A modification of the invention is illustrated in FIG. 12 and comprises a hollow adapter 106 having dimensions similar to the outer surface 36 of the end 32 of the suction probe 24 and a knob similar to the knob 38. A hollow projection 108 extends from the knob and is provided with an outer surface 110 over which the transparent tube 92 is positioned. Any type of means may be provided to insure a sealed relationship between the outer surface 110 and the transparent tube 92.

While the preferred embodiments of the invention have been illustrated and described herein, it may be otherwise embodied and practiced within the scope of the following claims.

What is claimed is:

1. A medical instrument for use in a Lipectomy procedure comprising:
   a handle having a longitudinal body portion and having a continuously closed first end portion and a second end portion located at substantially opposite ends of said longitudinal body portion, wherein said longitudinal body portion has dimensions so that said handle may be grasped securely by a user.
   a first projection extending from said closed first end portion of said handle, having means for being interchangeably connected to a source of vacuum or a medical probe;
   said first projection extending from said closed first end portion of said handle at a first predetermined angle and having a passageway extending therethrough;
   a second projection extending from said closed first end portion of said handle, having means for being interchangeably connected to a source of vacuum or a medical probe;
   said second projection extending from said closed first end portion of said handle at a second predetermined angle differing from said first predetermined angle of said first projection and having a passageway extending therethrough, wherein said passageway of said second projection adjoins said passageway of said first projection substantially adjacent to said continuously closed first end portion of said handle to permit substantially direct fluid communication therebetween; and
   valve means provided within said first projection for selectively opening and closing said passageway of said first projection.

2. A medical instrument as in claim 1 and further comprising:
   means for interconnecting either said first or second projection to a source of vacuum.

3. A medical instrument as in claim 2 wherein said interconnecting means comprises:
a transparent tube.

4. A medical instrument as in claim 3 and further comprising:
an adapter;
means at one end of said adapter for connecting said adapter to said first or second projection; and
a projection at the other end of said adapter over which said transparent flexible tube means may be secured in sealing engagement.

5. A medical instrument as in claim 4 wherein:
said connecting means of said adapter comprises a tapered outer surface on said one end of said adapter.

6. A medical instrument as in claim 5 wherein:
said projection of said adapter is provided with a conical outer surface having portions with diameters greater than the inner diameter of said transparent flexible tube means so that an effective seal is formed when said transparent flexible tube is pushed over said outer surface.

7. A medical instrument as in claim 2 and further comprising:
a medical probe having a predetermined shape and size;
said medical probe having a passageway extending therethrough and having an opening at a first and second end thereof; and
means at said first end of said medical probe for attaching said medical probe to said first or second projection.

8. A medical instrument as in claim 7 wherein a major portion of the length of said medical probe comprises a hollow tube; and
said opening at said second end of said medical probe is in a side wall of said tube.

9. A medical instrument as in claim 8 wherein said attaching means at said first end of said medical probe comprises:
a conical shaped surface surrounding said opening at said first end of said medical probe; and
said passageways of said first and second projections having inner surfaces for providing a sealed joint with said conical shaped surface.

10. A medical instrument as in claim 1 wherein:
the longitudinal axes of said handle and said first projection are in alignment; and
the longitudinal axis of said second projection extends at a predetermined angle to said longitudinal axes of said handle and said first projection.

11. A medical instrument as in claim 1 wherein said valve means comprises:
means in said first projection having a surface in sealing engagement with the inner surface of said first projection;
a passageway in said means in sealing engagement with said inner surface having a longitudinal axis coinciding with at least a portion of said longitudinal axis of said first projection;
means forming a cylindrical surface extending through said means in sealing engagement with said inner surface and intersecting said passageway;
a stem having an outer surface for engagement with said cylindrical surface;
a passageway extending through said stem and having a longitudinal axis extending at an angle of 90° to the longitudinal axis of said stem; and
means for rotating said stem to move said stem passageway into and out of fluid communication with said passageway in said means.

12. A medical instrument as in claim 11 and further comprising:
means for urging said stem into engagement with said cylindrical surface to provide frictional forces sufficient to hold said valve means in an opened or closed position but permitting rotation of said stem.

13. A medical instrument as in claim 12 wherein: said urging means comprises a spring.

14. A medical instrument as in claim 13 wherein said means forming a cylindrical surface comprises:
a tube having an inner cylindrical surface;
a pair of aligned openings in said tube; and
means for securing said tube in said means in said first projection so that said aligned openings are aligned with said passageway in said means in said first projection.

15. A medical instrument as in claim 11 and further comprising:
means for limiting said rotational movement to an open or close position.

16. A medical instrument as in claim 15 wherein:
the longitudinal axis of said second projection extends at an angle of about 45° from the longitudinal axis of said first projection.

17. A medical instrument as in claim 16 and further comprising:
a transparent flexible tube means for interconnecting either said first or second projection to a source of vacuum.

18. A medical instrument as in claim 17 wherein:
said first and second projections are provided with conical outer surfaces having portions with diameters greater than the inner diameter of said transparent flexible tube means so that an effective seal is formed when said transparent flexible tube is pushed over said outer surface of either the first or second projection.

19. A medical instrument as in claim 18 and further comprising:
means for urging said stem into engagement with said cylindrical surface to provide frictional forces sufficient to hold said valve means in an opened or closed position but permitting rotation of said stem;
a tube having an inner cylindrical surface;
a pair of aligned openings in said tube; and
means for securing said tube in said means in said first projection so that said aligned openings are aligned with said passageway in said means in said first projection.

* * * * *

UNITED STATES PATENT AND TRADEMARK OFFICE
CERTIFICATE OF CORRECTION

PATENT NO. : 4,568,332
DATED : February 4, 1986
INVENTOR(S) : Ronald D. Shippert It is certified that error appears in the above—identified patent and that said Letters Patent is hereby corrected as shown below:

At column 5, line 21, insert --means-- after the word tube.

Signed and Sealed this

Twenty-second Day of July 1986

[SEAL]

Attest:

DONALD J. QUIGG

*Attesting Officer*     *Commissioner of Patents and Trademarks*